(12) United States Patent
Phelps et al.

(10) Patent No.: US 7,998,072 B2
(45) Date of Patent: Aug. 16, 2011

(54) PROBE BASED DIGITIZING OR COMPRESSION SYSTEM AND METHOD FOR MEDICAL ULTRASOUND

(75) Inventors: Robert N. Phelps, Sammamish, WA (US); John C. Lazenby, Fall City, WA (US); David A. Petersen, Fall City, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 786 days.

(21) Appl. No.: 10/741,827

(22) Filed: Dec. 19, 2003

(65) Prior Publication Data
US 2005/0148878 A1    Jul. 7, 2005

(51) Int. Cl.
*A61B 8/00* (2006.01)
(52) U.S. Cl. ........ 600/437; 600/441; 600/443; 600/454; 600/462; 600/432; 310/334; 310/336
(58) Field of Classification Search .......... 600/440–447, 600/437, 459, 432, 454–456, 462; 128/661–662; 310/334, 336
See application file for complete search history.

(56) References Cited

U.S. PATENT DOCUMENTS

| | | | |
|---|---|---|---|
| H1171 H | | 4/1993 | Fillhart et al. |
| 5,267,221 A | | 11/1993 | Miller et al. |
| 5,348,014 A | | 9/1994 | Okado |
| 5,522,393 A | | 6/1996 | Phillips et al. |
| 5,538,004 A | * | 7/1996 | Bamber .................. 600/443 |
| 5,555,534 A | | 9/1996 | Maslak et al. |
| 5,573,001 A | | 11/1996 | Petrofsky et al. |
| 5,590,658 A | | 1/1997 | Chiang et al. |
| 5,617,866 A | | 4/1997 | Marian, Jr. |
| 5,622,177 A | * | 4/1997 | Breimesser et al. .......... 600/459 |

(Continued)

FOREIGN PATENT DOCUMENTS
CN         1342442 A      4/2002
(Continued)

OTHER PUBLICATIONS

"Fully Sampled Matrix Transducer for Real Time 3D Ultrasonic Imaging," by Bernard Savord, Rod Solomon—Philips Medical Systems, 300 Minuteman Rd., Andover MA; 9 pgs.; before Dec. 2003.

(Continued)

*Primary Examiner* — Brian Casler
*Assistant Examiner* — Joel M Lamprecht

(57) ABSTRACT

Methods, systems and probes communicate signals from a transducer for imaging or connection with an imaging system. Beamforming-related electronics are positioned in the connector housing of the transducer probe assembly. For example, analog-to-digital converters are positioned in the connector housing. Power is provided through connection with the ultrasound imaging system. Fans or other heat-dissipating structures are also positioned within the connector housing. Other beamformer electronics, such as delays and sums, are positioned in the imaging system, partly in the connector housing or entirely in the connector housing. Since the analog-to-digital converters are provided in the connector housing, partial digital beam forming may be provided in the transducer probe assembly. The length of the transducer cables is held constant to avoid interference and transmission line effects due to line-length variation. The number of cables and other interconnections from the transducer array to the analog-to-digital converters is unconstrained by the number of connectors or channels provided by the imaging system. Data compression provided by the electronics of the transducer probe assembly provides independence of the number of system channels from transducer channels.

21 Claims, 2 Drawing Sheets

U.S. PATENT DOCUMENTS

| | | | |
|---|---|---|---|
| 5,627,536 A * | 5/1997 | Ramirez | 341/141 |
| 5,676,147 A | 10/1997 | Petrofsky et al. | |
| 5,678,551 A * | 10/1997 | Stevens | 600/474 |
| 5,690,114 A | 11/1997 | Chaing et al. | |
| 5,817,024 A | 10/1998 | Ogle et al. | |
| 5,820,549 A | 10/1998 | Marian, Jr. | |
| 5,839,442 A | 11/1998 | Chaing et al. | |
| 5,957,846 A | 9/1999 | Chaing et al. | |
| 5,964,709 A | 10/1999 | Chiang et al. | |
| 5,997,479 A | 12/1999 | Savord et al. | |
| 6,013,032 A | 1/2000 | Savord | |
| 6,016,285 A * | 1/2000 | Wright et al. | 367/11 |
| 6,029,116 A | 2/2000 | Wright et al. | |
| 6,102,863 A * | 8/2000 | Pflugrath et al. | 600/447 |
| 6,106,472 A | 8/2000 | Chiang et al. | |
| 6,126,602 A | 10/2000 | Savord et al. | |
| 6,126,606 A | 10/2000 | Bergstoel | |
| 6,142,946 A | 11/2000 | Hwang et al. | |
| 6,248,073 B1 | 6/2001 | Gilbert et al. | |
| 6,371,918 B1 * | 4/2002 | Bunce | 600/459 |
| 6,375,617 B1 | 4/2002 | Fraser | |
| 6,491,634 B1 * | 12/2002 | Leavitt et al. | 600/447 |
| 6,530,887 B1 | 3/2003 | Gilbert et al. | |
| 6,537,219 B2 * | 3/2003 | Poland et al. | 600/447 |
| 6,540,685 B1 | 4/2003 | Rhoads et al. | |
| 6,544,175 B1 | 4/2003 | Newman | |
| 6,575,908 B2 | 6/2003 | Barnes et al. | |
| 6,582,367 B1 | 6/2003 | Robinson et al. | |
| 6,589,179 B2 | 7/2003 | Criton et al. | |
| 6,612,987 B2 | 9/2003 | Morsy et al. | |
| 6,629,928 B1 | 10/2003 | Dolan et al. | |
| 6,635,019 B2 | 10/2003 | Davidsen | |
| 6,648,826 B2 | 11/2003 | Little et al. | |
| 6,814,701 B1 | 11/2004 | Tamura | |
| 6,875,178 B2 | 4/2005 | Phelps et al. | |
| 6,932,517 B2 | 8/2005 | Swayze et al. | |
| 7,115,093 B2 * | 10/2006 | Halmann et al. | 600/437 |
| 7,371,218 B2 | 5/2008 | Walston et al. | |
| 2003/0139664 A1 | 7/2003 | Hunt et al. | |
| 2004/0015079 A1 * | 1/2004 | Berger et al. | 600/437 |
| 2004/0109028 A1 | 6/2004 | Stern et al. | |
| 2004/0133110 A1 * | 7/2004 | Little et al. | 600/457 |
| 2004/0181154 A1 | 9/2004 | Peterson et al. | |
| 2005/0148873 A1 | 7/2005 | Petersen et al. | |
| 2005/0192499 A1 | 9/2005 | Lazenby et al. | |
| 2005/0203391 A1 | 9/2005 | Phelps et al. | |
| 2005/0203404 A1 | 9/2005 | Freiburger | |
| 2008/0027322 A1 | 1/2008 | Freiburger | |
| 2008/0027323 A1 | 1/2008 | Freiburger | |

FOREIGN PATENT DOCUMENTS

| | | |
|---|---|---|
| EP | 1049407 B1 | 12/2005 |
| WO | WO 00/30540 | 6/2000 |

OTHER PUBLICATIONS

Office Action, dated Oct. 5, 2007, for US 20050148873 A1 (U.S. Appl. No. 10/741,538).

"Fully Sampled Matrix Transducer for Real Time 3D Ultrasonic Imaging," by Bernard Savord, Rod Solomon—Philips Medical Systems, 300 Minuteman Rd., Andover MA; 9 pgs.; before Dec. 2003.

* cited by examiner

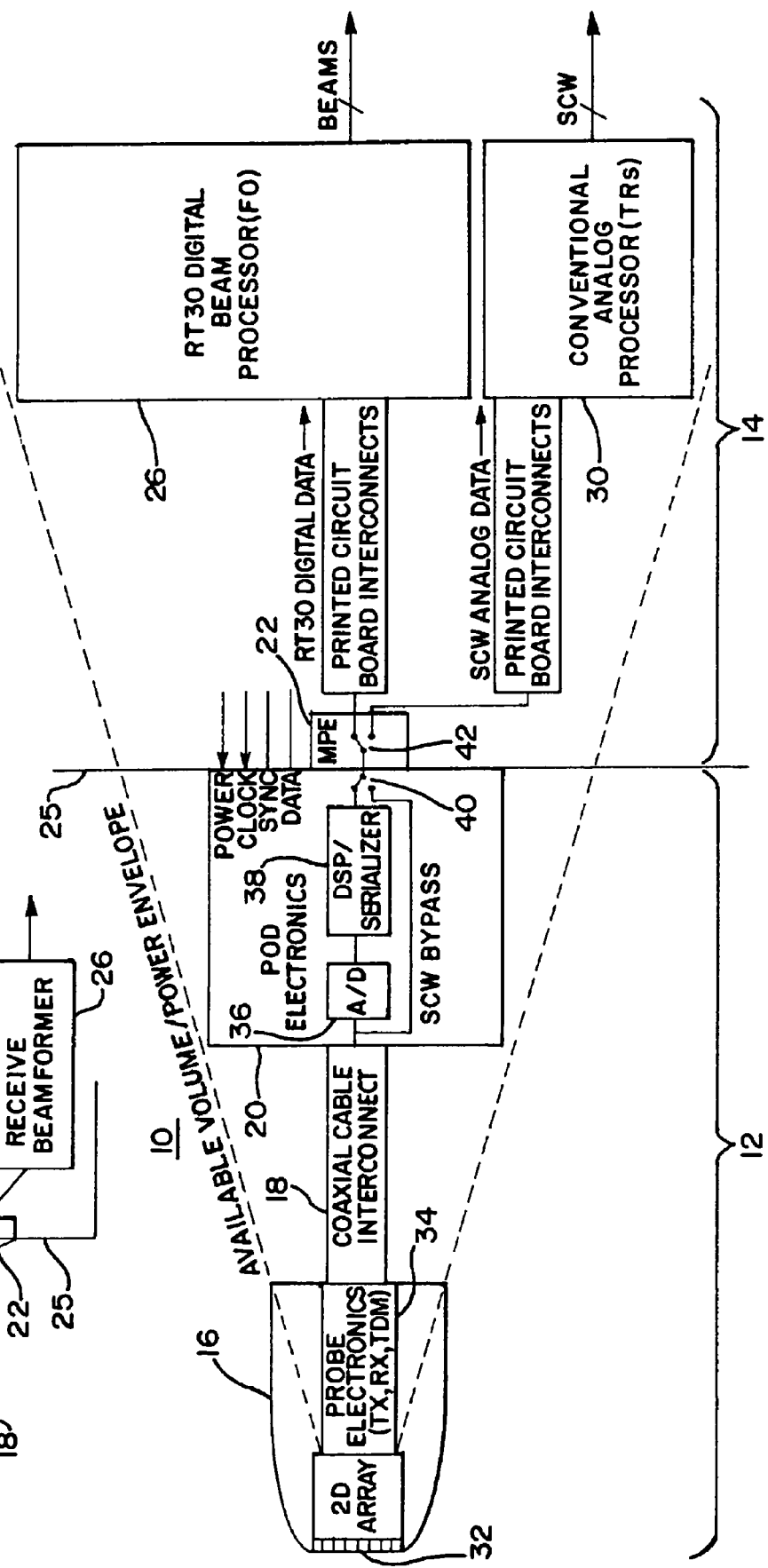

PROBE BASED DIGITIZING OR COMPRESSION SYSTEM AND METHOD FOR MEDICAL ULTRASOUND

BACKGROUND

The present invention relates to transducer architectures and ultrasound systems. In particular, electronics are positioned in an ultrasound transducer probe assembly.

Medical diagnostic ultrasound systems typically have detachable ultrasound probe assemblies. A transducer array is housed in a hand-held probe. The hand-held probe is connected through a cable to a connector housing. The connector housing electrically and mechanically releasably connects to an ultrasound system. The user can select different ultrasound probes for different examinations and connect the selected probe to the ultrasound imaging system. Using beamformers and other circuitry in the ultrasound imaging system, an image is generated through the transmission and reception of acoustic energy by the connected transducer probe.

Electronics associated with the imaging system have been placed in the ultrasound probe housing. For example, U.S. Pat. No. 5,590,658 discloses a hand-held probe housing in which the ultrasonic transducers and beam forming circuitry are housed. As another example, U.S. Published Pat. application Ser. No. 20040002652, the disclosure of which is incorporated herein by reference, discloses integrating a multiplexer and other electronics in the hand-held ultrasound transducer probe housing. Signals from a plurality of transducer elements are time division multiplexed onto a few number of cables for transmission to the ultrasound imaging system. In another ultrasound transducer probe assembly, a controller for a wobbler transducer is positioned in the connector housing for controlling the motor of the wobbler array in the probe housing.

BRIEF SUMMARY

By way of introduction, the preferred embodiments described below include methods, systems and probes for communicating signals from a transducer for imaging or connection with an imaging system. Beamformer-related electronics are positioned in the connector housing of the transducer probe assembly. For example, analog-to-digital converters are positioned in the connector housing. Power is provided through connection with the ultrasound imaging system. Fans or other heat-dissipating structures are also positioned within the connector housing. Other beamformer electronics, such as delays and sums, are positioned in the imaging system, partly in the connector housing or entirely in the connector housing. Since the analog-to-digital converters are provided in the connector housing, partial digital beam forming may be provided in the transducer probe assembly. The length of the transducer cables is held constant to avoid interference and transmission line effects due to line-length variation. The number of cables and other interconnections from the transducer array to the analog-to-digital converters is unconstrained by the number of connectors or channels provided by the imaging system. Data compression provided by the electronics of the transducer probe assembly provides independence of the number of system channels from transducer channels. In alternative embodiments, the analog-to-digital converters are positioned in the transducer probe housing.

In a first aspect, an ultrasound probe for connection with an imaging system is provided. A releasable connector electrically connects with an ultrasound transducer. The releasable connector releasably connects with an ultrasound imaging system. The releasable connector has a plurality of electrical outputs for respective signals representing different elements individually or by groups. An analog-to-digital converter connects between the ultrasound transducer and the releasable connector.

In a second aspect, a system for communicating signals from a transducer is provided for imaging. The system includes a processing system and a detachable transducer assembly. The processing system has a receive beamformer, a system housing and a connector on the system housing. The connector electrically connects with the receive beamformer. The detachable transducer assembly includes a transducer probe at least partially housing an array of elements, a connector housing at least partially housing an analog-to-digital converter, and at least one cable connecting the transducer probe with the connector housing. The connector housing is physically connectable and detachable from the connector on the system housing.

In a third aspect, an ultrasound probe for connection with an imaging system is provided. A releasable connector electrically connects with an ultrasound transducer and is releasably connectable with an ultrasound imaging system. The releasable connector has a plurality of electrical outputs for respective signals representing different elements individually or by groups. A processor connects between the ultrasound transducer and the releasable connector. The processor is spaced away from the ultrasound transducer and adjacent to the releasable connector. The processor is operable to compress signals from the ultrasound transducer.

In a fourth aspect, a method for communicating signals from a transducer array to an imaging system is provided. A probe assembly is releasably connected to an imaging system. Acoustic energy is transduced into electrical signals. The electrical signals are transmitted to an analog-to-digital converter. The electrical signals are converted into digital data within the probe assembly. The digital data is passed from the probe assembly to a beamformer of the imaging system.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like-reference numerals designate corresponding parts throughout the different views.

FIG. 1 is a block diagram of one embodiment of a system for communicating signals from a transducer for imaging;

FIG. 2 is another embodiment of a system for communicating signals from a transducer to a system;

DETAILED DESCRIPTION OF THE DRAWINGS AND PRESENTLY PREFERRED EMBODIMENTS

Figure 4:
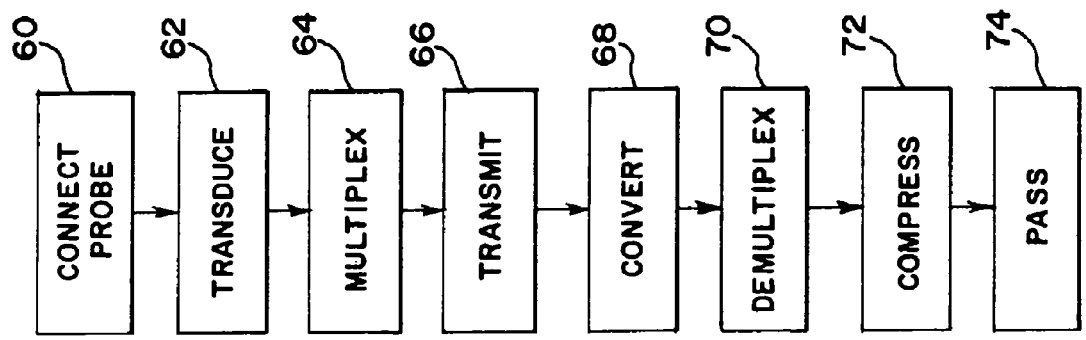
FIG. 4 is a flow-chart diagram of one embodiment of a method for communicating signals from a transducer.

Various advantages and combinations of devices are provided in different embodiments. The embodiments may include none, one or multiple of the advantages and structures discussed herein. For example, a transducer probe assembly allows high bandwidth time-division multiplexed data to be generated in the transducer handle or probe housing and digitized in the transducer pod or connector housing. The transmission paths between multiplexing and digital conversion are matched in length and impedance, avoiding mismatches and variation in intersymbol interference from one path to the next. A noise-resistant digital path from the transducer assembly connector to the beamformer electronics of the imaging system beamformer is also provided. In alternative embodiments, analog-to-digital conversion is provided within the transducer probe assembly without time division multiplexing. Using compression electronics in the transducer probe assembly, more transducer elements than beamformer channels may be provided. The compression electronics compresses the data from the multiple elements onto signal lines or channels for the beamformer. In yet another embodiment, analog pass-through switching is provided for allowing both analog and digital outputs by the transducer probe assembly. Since the transducer probe assembly outputs digital data, digital signals representing acoustic information received at each element is provided for research, experimentation or transmission to remote work stations for imaging free of previous beamforming or with minimal previous beamforming. Digitizing signals within the transducer probe assembly may eliminate cross-talk and other interferences provided in non-coaxial transmission paths, allowing transmission through components other than space-consuming coaxial cables.

FIGS. 1 and 2 show one embodiment of a system 10 for communicating electrical signals from a transducer probe assembly 12 to a processing system 14. FIG. 1 shows the transducer probe assembly 12 disconnected from the processing system 14, and FIG. 2 shows the transducer probe assembly 12 connected to the processing system 14. The detachable transducer probe assembly 12 allows selection of different transducers with different frequency responses or other characteristics for imaging with the processing system 14.

The processing system 14 is a medical diagnostic ultrasound imaging system in one embodiment. In other embodiments, the imaging system 14 is a computer, workstation or other medical imaging system. For an ultrasound system, the processing system 14 includes a transmit beamformer 24 and a receive beamformer 26 connected with a connector 22. The transmit beamformer 24 is operable to generate a plurality of relatively delayed and apodized waveforms for transmitting acoustic energy along one or more beams at the same time. The electrical signals generated by the transmit beamformer 24 are routed to the connector 22. The connector 22 also electrically connects to the receive beamformer 26. In one embodiment, the connections within the processing system 14 from the connector 22 are permanent and made through one or more switches, such as a transmit and receive switch.

The receive beamformer 26 is an analog or digital receive beamformer. The receive beamformer 26 is configured to receive digital signals, but may be configured to receive either analog or digital signals. In one embodiment, the receive beamformer 26 includes separate beamformers for either analog or digital data or as a function of imaging mode, such as a separate spectral Doppler beamformer and a B-mode and color-flow mode beamformer. For example, the receive beamformer 26 is a digital processor on a card, ASIC or other device, and a separate analog processor for continuous wave signals is provided on a separate card as processor 30 shown in FIG. 2. The beamformer 26 includes a plurality of delays, amplifiers and one or more summers. The electrical signals representing different elements or groups of elements are relatively delayed, apodized and then summed to form samples or signals representing different spatial locations along one or more receive beams. The beamformers are configured to provide a wideband interface, such as a switching matrix with 384-wire impedance controlled paths from the connector 22 to the beamforming cards or slots on the printed circuit board interconnects. Other switching matrix and number of paths may be provided. The receive beamformer 26 may be distributed, such as different parts of the beamformer in different locations within the processing system 14 or external to the processing system 14 (e.g., a portion of the receive beamformer 26 within the transducer probe assembly 12).

Further processes and associated circuitry are implemented by the processing system 14 for generating an image or for calculating measurements from the receive beamformed information. Different, additional or fewer transmit and receive circuit devices or components may be provided.

The transmit beamformer 24, receive beamformer 26 and connector 22 are at least partially enclosed within a system housing 25. The system housing 25 is plastic, metal, wood, fiberglass, or any other now-known or later-developed material for housing electronics. In one embodiment, the system housing 25 is a workstation or cart-based housing supported on wheels or resting on the floor. In other embodiments, the system housing 25 is a laptop or other portable-sized device, such as a suitcase-sized portable ultrasound system. In yet another embodiment, the system housing 25 is a hand-held ultrasound system, such as a PDA or scope-shaped housing.

The connector 22 is one of any now-known or later-developed mechanical and electrical connectors for detachably connecting and removing the transducer probe assembly 12. The connector 22 includes grooves, extensions, latches, screws, threaded holes or any other now-known or later-developed mechanical structure for releasably connecting to another device. A plurality of male or female electrical connections for connecting with individual digital traces, such as in a circuit board configuration, or for connecting with coaxial cables is provided. For example, 192 or other number of electrical connections of exposed metallic traces on a circuit board for mating are recessed within the connector 22. In one embodiment, the connector disclosed in U.S. Pat. No. 6,371,918, the disclosure of which is incorporated herein by reference, is used.

The connector 22 mounts to the system housing 25. While one connector 22 is shown, a plurality of different connectors may be provided for connecting to a same type or different types of transducer probe assemblies 12. The connector 22 electrically connects with the receive beamformer 26 for communicating analog or digital signals. In alternative embodiments, the connector 22 is a standard or custom connection on a PC, digital repeater or other electrical device for locally processing data or for transmitting data for remote processing.

In one embodiment shown in FIG. 2, the connector 22 includes one or more switches 42, such as a multiplexer, group of transistors or other switching device for switching one or more inputs from the connector 22 to different receive beamformers 26, 30 or different channels of a given receive beamformer 26 or 30. In other embodiments, the switch 42 for switching between receive beamformers or channels is provided by components separate from the connector 22 or is not provided.

The ultrasound transducer probe assembly includes a transducer probe housing 16, a cable 18, and a connector housing 20. Additional, different or fewer components may be provided. For example, a hand-held system 10 is provided where the transducer probe housing 16 is included as part of the connector housing 20 without the cable 18. The transducer probe assembly 12 provides a detachable transducer.

The transducer probe housing 16 is plastic, metal, rubber, combinations thereof or any other now-known or later-developed material for housing a transducer array of elements 32. In one embodiment, the transducer probe housing 16 is shaped for hand-held use. In other embodiments, the transducer probe housing 16 is shaped for use internal to a patient, such as shaped as an endoscope or catheter. The transducer probe housing 16 at least partially houses an array of elements, such as covering a portion of the array and allowing a face of the array acoustical access for scanning a patient.

The array of elements 32 is an array of piezoelectric, capacitive membrane ultrasound transducer or other now-known or later-developed elements for converting between electrical and acoustical energies. One or two-dimensional arrays are provided with full or sparse sampling. For example, a 2-dimensional array has 1,920 or other number of fully-sampled elements in a square or rectangular grid positioned on a planer or curved surface. The transducer array 32 includes a flex circuit, signal traces or other structures for electrical interconnection from the elements of the array 32 to other electronics of the probe assembly 12. For example, the flex circuits are connected to a plurality of coaxial cables in the cable 18 or to electronics within the connector housing 20.

In an alternative embodiment, the transducer array 32 electrically connects to electrical components 34 within the probe housing 16. For example, the probe electronics 34 include a multiplexer electrically connected between the plurality of cables of the cable 18 and the transducer elements of the array 32. The multiplexer is positioned in the transducer probe housing 16 with the array 32. The multiplexer is operable to multiplex signals from a plurality of elements onto a fewer number of outputs using time division multiplexing. In alternative embodiments, other forms of multiplexing are provided. Preamplifiers or other structures are also included in other embodiments with the multiplexer. For example, the structures disclosed in U.S. Published Pat. application Ser. Nos. 20040002652 and 20030139671 the disclosures of which are incorporated herein by reference, are used. For a multidimensional array, signals from every 2, 4, 8 or other number of elements are multiplexed onto a common output. A plurality of outputs for different groups of elements is provided. In alternative embodiments, the probe electronics 34 are different components for the same or different functions, or the transducer probe housing 16 is provided without the further electronics 34. In another embodiment, the probe electronics 34 include delays, amplifiers and summers for performing beamforming functions for sub-arrays or across the entire array.

The cable 18 includes a plurality of coaxial cables. For example, 64, 128, 192 or other number of coaxial cables are provided for transmitting electrical signals representing acoustic energy received at elements of the array 32. Each coaxial cable receives information for one element or multiplexed information representing a plurality of different elements. In alternative embodiments, the cable 18 is a flexible circuit, optical data path, fiber optic, insulated wires or other now-known or later-developed structure. For example, analog-to-digital converters are provided in the transducer probe housing 16, and digital signals are transmitted along now-known or later-developed digital paths through the cable 18. The cable 18 electrically connects the ultrasound transducer array 32 to the electronics of the connector housing 20, such as an analog-to-digital converter 36. The plurality of coaxial cables or other signal lines within the cable 18 electrically connect the transducer elements of the array 12 to a respective or different number of analog-to-digital converters 36. Where multiplexing is provided, fewer cables than elements may be used.

Figure 3:
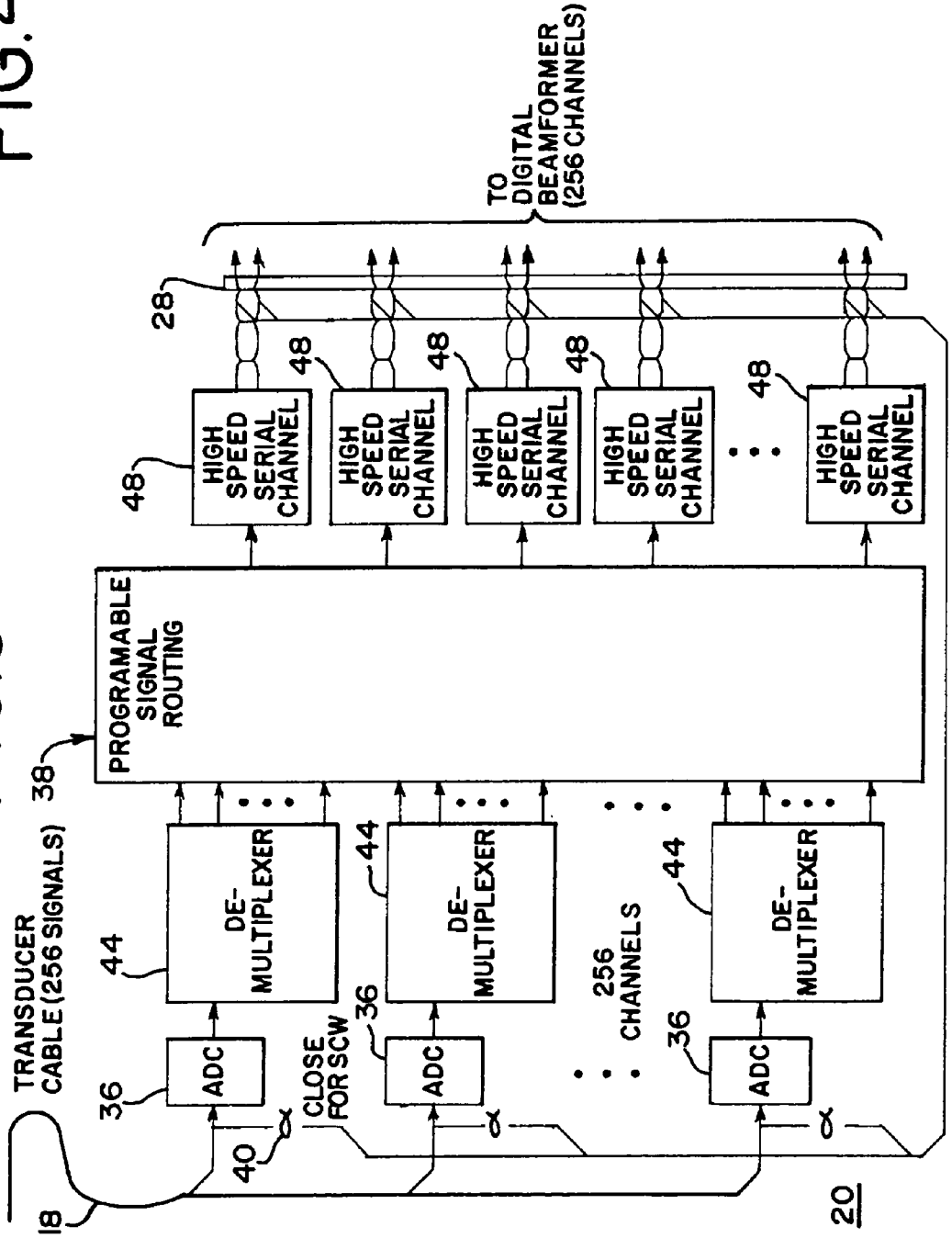
FIG. 3 is a block diagram of one embodiment of the circuitry in a transducer probe assembly connector housing.

The connector housing 20 is metal, plastic, rubber, combinations thereof or other now-known or later-developed materials for housing or at least partially housing the analog-to-digital converter 36, digital processor 38, switch 40, and a releasable connector 28. Additional, different or fewer components may be included within the connector housing 20. For example, demultiplexers 44 and serializers 48 shown in FIG. 3 are additionally housed within the connector housing 20. As another example, the analog-to-digital converter 36 or digital processor 38 are positioned within the probe housing 16 rather than the connector housing 20. The connector housing 20 is connected at the end of the cable 18, so that the connector housing 20 is spaced from the ultrasound transducer array 32 and associated probe housing 16.

The connector housing 20 is shaped to allow detachment and attachment to the housing 25 of the processing system 14. In one embodiment, now-known connector housings are extended in length away from the connector 28 to accommodate the additional electronics, such as extending by twice the distance used for connectors without electronics. Different changes in dimension may be provided, such as making the connector housing 20 longer, higher, wider or combinations thereof. The connector housing 20 is shaped and sized to include heat sinking, fans and/or active cooling for cooling the enclosed electronics. In alternative embodiments, no additional cooling devices or different now-known or later-developed cooling is provided. In one embodiment, at least one fan is positioned adjacent to a vent in the connector housing 20. Additionally or alternatively, a rigid thermal connection is provided between the connector housing 20 and the processing system 14 for conducting heat away from the electronics. A forced air connection between the connector housing 20 and the processing system 14 may alternatively be provided for ducting hot air from the connector housing 20 through a fan in the processing system 14 or forcing air from the processing system 14 into the connector housing 20.

FIG. 3 shows one embodiment of the electronics within the connector housing 20. A plurality of analog-to-digital converters 36 are connected to a respective plurality of demultiplexers 44. The demultiplexers 44 connect to a digital processor 38, and a plurality of high-speed serializers 48. Additional, different or fewer components may be provided. In one embodiment, one or more of the components are combined into a single processor, such as providing demultiplexers 44 and the digital processor 38 on a single application-specific integrated circuit.

Additional components may be provided in the connector housing 20. For example, termination resistors connect with each of the cables for providing an impedance match. Alternatively, amplifiers of the analog-to-digital converters 36 provide impedance matches to the cables. The transmit path is provided by switches (e.g., multiplexer or transistor) to bypass the digital processing of the receive circuitry and connect to the cable 18. Alternatively, a portion or all of the transmit beamformer is provided within the transducer probe assembly 12.

The switch 40 is a transistor, multiplexer or other now-known or later-developed switch for routing analog or digital signals on the cable 18 around all or some of the electronics in the connector housing 20. The switch 40 is positioned between the transducer array 32 and the analog-to-digital converter 36 for bypassing analog signals from the signal lines of the cable 18 to a respective plurality of electrical outputs of the connector 28. In alternative embodiments, the switch 40 is not provided or additional switches for more selectable routing are provided.

The analog-to-digital converters 36 are processors, application-specific integrated circuits, digital components, analog components, amplifiers, transistors, combinations thereof or other now-known or later-developed devices for converting analog information to digital samples. One analog-to-digital converter 36 is provided for each of the signal lines of the cable 18, or one analog-to-digital converter 36 may be used for multiple of the signal lines. Any number of bits of resolution may be provided by the analog-to-digital converter, such as 4, 8 or 10-bits. Any sampling rate may be used, such as sampling at four times the center frequency of the transducer array 32 on a time-division multiplexed output line (e.g., 96 megasamples per second). In one embodiment, each analog-to-digital converter 36 is a single device or is a package or chip including analog-to-digital converters 36 for 16 to 32 time-division multiplexed channels. At 32 channels per chip, 256 channels of analog-to-digital conversion are provided by 8 devices. Each chip may have 672 pins and be 45 mm on a side with a die size of 12.8 by 12.8 mm. Other size chips and associated analog-to-digital conversion structures may be used. The analog-to-digital converters 36 connect between the ultrasound transducer array 32 and the releasable connector 28. Each of the analog-to-digital converters 36 whether in a same or different chip connects with different ones of the plurality of transducer elements. For example, one analog-to-digital converter 36 connects with one element. As another example, one analog-to-digital converter 36 connects with a group of elements with time-division multiplexed signals output on a same line. Different analog-to-digital converters 36 connect with different elements or groups of elements. To reduce power consumption of a plurality of analog-to-digital converters 36, a slightly lower than rated sampling rate may be used, but a full sampling rate may be provided, such as providing for 10-bit sampling at 120 megasamples per second with a power dissipation of about 50 milliwatts.

The demultiplexers 44 are application-specific integrated circuits, multiplexers or other now-known or later-developed devices for demultiplexing time division or other multiplexed information. The demultiplexers 44 connect with the output of the analog-to-digital converters 36 for providing signals representing specific single or small groups of elements separately. In alternative embodiments, the demultiplexers are positioned prior the analog-to-digital converters 36 or not provided.

The digital processor 38 is an application-specific integrated circuit, transistors, multiplexer, switches, delays, amplifiers, summers, digital circuit, analog circuit, combinations thereof or other now-known or later-developed digital signal processing device. In one embodiment, the digital processor 38 provides data compression, such as where the number of elements of the transducer array 32 is greater than the number of separate electrical connections between the connector 28 and the connector 32 of the processing system 14. The processor 38 is connected between the analog-to-digital converters 36 and the electrical outputs of the connector 28. Digital data is provided as an input for processing, such as partial beamforming operable to combine data from elements of the transducer array and output the combined data on respective ones of the plurality of electrical outputs of connector 28. For example, data from subarrays of elements are combined and output as a single data stream. Separate data streams are output for different elements or subarrays. The partial beamformer implemented by the processor 38 connects with the analog-to-digital converters 36 to combine signals from at least two elements of the transducer array 32. By compressing the data, the number of transducer elements used may be independent of the number of system connections or channels of the processing system 14. The processor 38 may additionally perform synthetic aperture operations, such as acquiring the ultrasound aperture in several time-spaced acquisition cycles and synthetically creating the image as though it came from a single acquisition cycle.

Alternatively, demultiplexing 44 is provided in the processing system 14 without further data compression performed by the electronics within the connector housing 20. For example, the connector 22 provides 192 differential pairs each capable of supporting 0.8 gigabits per second of data transmission. An aggregate bandwidth for the connector 22 is provided as 154 gigabits per second. At 10 megasamples per second with an 8-bit data width, 1,920 elements may be supported. Operating at a 2.5 megahertz center frequency, fully-sampled multi-dimensional array may be used. More or fewer cables with a lesser or greater time-division multiplex ratio may be used.

As an alternative to continuing the time-division multiplexing in the digital data, the embodiment of FIG. 3 provides for demultiplexing with demultiplexers 44 and further compression by partial beamforming. Using delays and sums, signals from a two by two or other size subarray are combined. By combining two by two subarrays, a factor of four data compression results. The steering direction is assumed or is controlled as a function of time for implementing the delays. Where the subarrays are adjacent elements, the total amount of delay may be small, but larger subarrays may be provided with corresponding larger compression rates and associated delays. In the embodiment of FIG. 3, the tradeoff between amount of compression, the number of probe channels and the number of system channels provides freedom of operation. For example, the time-division multiplexing rate and number of probe channels is chosen optimally for a given available technology. The time-division multiplexing rate is traded for analog-to-digital conversion sampling frequency. As the state-of-the-art of analog-to-digital converters provides increased performance, greater time-division multiplexing and associated compression may be provided.

In an alternative embodiment, the processor 38 is provided with or without the analog-to-digital converters 36. For example, the processor 38 is connected between the ultrasound transducer array 32 and the releasable connector 28. The processor 38 is operable to compress analog signals from the ultrasound transducer. The processor 38 is positioned within the connector housing 20.

The serializers 48 are application-specific integrated circuits, digital signal processors, bus controllers, field-programmable gate arrays (FPGA), digital circuits, analog circuits or other now-known or later-developed device for providing serial output of data for each of a plurality of channels. A wideband interface with a high sampling rate is provided, such as providing a serializer 48 for each of 128, 192, 256 or other number of beamformer channels of the processing system 14. Using an FPGA, a single device may provide 20 or more serializers or deserializers. If an FPGA is configured for only serializers and operated at a lesser speed, power is conserved and a fewer number of chips or space is used by the serializers 48. Each of the serializers 48 connects directly or through one or more circuits with the demultiplexers and provides an output to one or more of the plurality of electrical outputs on the connector 28. Digital data provided by the analog-to-digital converters 36 is provided through the serializers 48 to the connector 28. In other embodiments, parallel or other data output schemes are provided.

The releasable connector 28 electrically connects with the ultrasound transducer array 32 without any detachable connections. Alternatively, one or more detachable connections is provided, such as at the interface between the cable 18 and the probe housing 16. The connector 28 is releasably connectable with the processing system 14. The connector 28 includes mechanical and electrical structures corresponding to the mechanical and electrical structures of the connector 22 of the processing system 14. For example, a plurality of electrical signal lines for connection with exposed traces on a circuit board protrudes from the connector housing 20 for insertion into the connector 22. The connectors 22, 28 include power, clock, synchronization or other control lines for implementing the digital processing within the connector housing 20 or the transducer probe assembly 12 in synchronization with a format usable by the processing system 14. Latches, extensions, screws, threaded holes or other now-known or later-developed releasable connection structures are provided for mechanically attaching the connectors 28 and 22. Electrical outputs or connections are provided for each of the serializer outputs or signals representing different elements. In one embodiment, the connector 28 is a connector as disclosed in U.S. Pat. No. 6,371,918. Different connectors may be provided. The connector 28 and 22 are operable to easily detach and attach. Through rotation, latching or other processes, the connectors 22, 28 are attached or detached in seconds or tens of seconds. Longer time periods may be used for more solid connections or for different connectors.

The electrical outputs of the connector 28 are also connected to the cables 18 through the switches 40 for routing analog signals to the outputs. For continuous wave operation, the dynamic range may best be communicated through analog signals. By passing the analog signals from the transducer array 32 to the analog beamformer 30, sufficient dynamic range may be provided. No further processing is provided in the connector housing 20, but some beamformation or delay and sum operations may be provided. Continuous wave summation provides for relative delays rather than absolute delays. Analog or digital circuitry is provided for summing so that the number of signals output from the connector 28 matches the number of system channels of the connector 22 even with a different number of signal lines within the cable 18 or elements of the array 32. Signals with the same phase are summed together to reduce the signal count. To protect the digital circuitry, the serializer outputs are tri-stated so that the gates are turned off or an open circuit is provided to avoid damage to digital circuitry. Opening of the switches 40 prevents feedback of the digital signals output by the serializers 48 to the cables 18 or other circuitry.

In one embodiment, a standard digital interface is provided on a plurality of different processing systems 14 by the same or different manufacturers. Digital processing provided in the transducer probe assembly 12 provides signals output pursuant to the digital standard interface. Data compression or rapid scanning techniques, such as plane wave transmissions followed by received beamformation over a large area, may be provided. One embodiment is shown above for FIG. 3, but different embodiments using a same or different components, number of components, type of components, relative positioning of components or other alterations may be provided.

FIG. 4 shows a method for communicating signals from a transducer array to an imaging system. The method of FIG. 4 is implemented using the systems of FIG. 1, 2 or 3. In alternative embodiments, different systems are used. Additional, different or fewer acts than described below for FIG. 4 may be used.

In act 60, a probe is connected to an ultrasound imaging system. For example, a user selects a transducer probe assembly and inserts a connector of the probe assembly into or onto an imaging system. The connector is then latched through rotation of a latch mechanism. After configuring the imaging system, transmit signals are provided through the releasable connection to the ultrasound transducer of the connected probe assembly. The transducer converts the electrical signals into acoustic energy for scanning the patient in act 62. In response to the transmitted acoustic energy, echo signals reflect back to the transducer. A plurality of elements receives echo signals and converts the echo signals into analog electrical signals.

In optional act 64, the received electrical signals of each or some of the plurality of elements in the receive aperture are multiplexed. Any of various multiplexing ratios may be used, such as multiplexing 2, 4, 8, 16, 32 or other number of transducer element channels onto a same output. Using time division, frequency coding, spread spectrum or other multiplexing scheme, each combined signal path represents a plurality of different elements. Whether multiplexed or not, the output signals are transmitted in act 66. The transmission is along a plurality of cables or other signal lines. The transmission is of analog signals in one embodiment, but digital signals may be transmitted in other embodiments.

In act 68, the received analog signals are converted into digital signals. The conversion occurs within the transducer probe assembly, prior to the signals passing through the detachable or releasable connection. For example, the analog signals are transmitted through a cable of the detachable probe assembly. The electrical signals are converted into digital data within a connector housing of the probe assembly.

In optional act 70, the digital data is demultiplexed prior to passing the digital data from the probe assembly to a beamformer of the imaging system. The demultiplexing is performed on digital data after conversion, but alternatively is performed on analog signals prior to conversion.

In optional act 72, the digital data is compressed. For example, previous multiplexing is preserved without demultiplexing or the demultiplexed digital data is then re-multiplexed using a same or different multiplexing scheme or format. As another example, partial beamforming is performed by summing signals within subarrays. Other digital data compression schemes may be used, including now-known or later-developed digital compression processing (e.g., MPEG, lossy and/or non-lossy). In alternative embodiments, the compression is performed on analog signals.

In act 74, the digital data with or without compression is passed from the probe assembly to a beamformer of the imaging system. Digital data passes through the releasable connector for further imaging or calculations. Any of various formats may be used, including serial or other connections. Due to the compression, the number of elements and associated channels within the transducer probe assembly may be different than the number of channels of the connector or imaging system. Alternatively or additionally, analog signals are passed from the probe assembly to the imaging system.

While the invention has been described above by reference to various embodiments, it should be understood that many changes and modifications can be made without departing of the scope of the invention. For example, any of the components, schemes, embodiments or other features disclosed in U.S. Published Pat. Application Ser. No. 20050148873, filed herewith, the disclosure of which is incorporated by reference, may be used for or with analog-to-digital conversion and/or compression. It is therefore intended that the foregoing detailed description be regarded as illustrative rather than limiting and that it is the following claims, including all equivalents, which are intended to define the spirit and the scope of this invention.

We claim:

1. An ultrasound probe for connection with an imaging system, the probe comprising:
   an ultrasound transducer;
   a releasable connector electrically connected with the ultrasound transducer and releasably connectable with an ultrasound imaging system, the releasable connector having a plurality of electrical outputs for respective signals each representing one or more different elements;
   an analog-to-digital converter connected between the ultrasound transducer and the releasable connector and separate from the ultrasound imaging system and an imaging system housing;
   a coaxial cable electrically connecting the ultrasound transducer to the analog-to-digital converter, the coaxial cable having a length longer than a longest dimension of a probe housing housing the ultrasound transducer; and
   a connector housing connected with an end of the coaxial cable, at least part of the coaxial cable outside of the connector housing and the probe housing, and the connector housing at least partially around the releasable connector and the analog-to-digital converter, the housing spaced from the ultrasound transducer;
   wherein the releasable connector mates with and is releasable from the imaging system housing, and the coaxial cable is non-releasably connected with the connector housing, the connector housing positionable against the imaging system housing when the releasable connector mates with the imaging system housing and when the releasable connector is connected for communicating from the analog-to-digital converter to the ultrasound imaging system, the connector housing having a lesser volume than the imaging system housing.

2. The probe of claim 1 wherein the ultrasound transducer comprises a multi-dimentional array of elements.

3. The probe of claim 1 wherein the ultrasound transducer comprises a plurality of transducer elements, the analog-to-digital converter electrically connected with at least a first element of the plurality of transducer elements;
   further comprising a plurality of analog-to-digital converters, the plurality of analog-to-digital converters including the analog-to-digital converter electrically connected with the first element, the plurality of analog-to-digital converters electrically connected with different ones of the plurality of transducer elements.

4. The probe of claim 3 further comprising:
   a plurality of coaxial cables electrically connecting the plurality of transducer elements to the respectively plurality of analog-to-digital converters, the plurality of coaxial cables being fewer than the plurality of transducer elements; and
   a multiplexer electrically connected between the plurality of coaxial cables and the plurality of transducer elements.

5. The probe of claim 1 further comprising:
   a summer connected with the analog-to-digital converter, the summer operable to combine signals from at least two elements of the ultrasound transducer, the combined signal output on one of the plurality of electrical outputs as a signal representing one of the different elements.

6. The probe of claim 1 further comprising a partial beamformer operable to combine data from elements of the ultrasound transducer and output the combined data on respective ones of the plurality of electrical outputs.

7. The probe of claim 1 further comprising:
   a digital processor connected between the analog-to-digital converter and one of the plurality of electrical outputs.

8. The probe of claim 1 further comprising:
   a switch connected between the ultrasound transducer and the analog-to-digital converter, the switch operable to bypass analog signals to one of the plurality of electrical outputs.

9. The probe of claim 1 further comprising:
   a demultiplexer connected with the analog-to-digital converter; and
   a serializer connected with the demultiplexer and at least one of the plurality of electrical outputs.

10. A system for communicating signals from a transducer for imaging, the system comprising:
    a processing system comprising:
       at least a part of a receive beamformer;
       a system housing; and
       a connector on the system housing, the connector electrically connectable with the receive beamformer; and
    a detachable transducer assembly comprising:
       a transducer probe at least partially housing an array of elements;
       a connector housing at least partially housing an analog-to-digital converter, the connector housing physically connectable and detachable from the connector on the system housing, the connector housing abutting against the imaging system housing when mated with the imaging system housing and when connected for communicating from the analog-to-digital converter to the receive beamformer; and
       at least one cable connecting the transducer probe with the connector housing, the connector housing being separate from the transducer probe housing the array and the cable extending between the transducer probe and the connector housing outside of both the connector housing and the transducer probe, the cable non-releasably connected with the connector housing and the transducer probe.

11. The system of claim 10 wherein the transducer probe is a handheld probe.

12. The system of claim 10 wherein:
    the transducer probe further houses a multiplexer connected with a plurality of the elements of the array, the multiplexer operable to multiplex signals from the plurality of elements to an output; and
    the connector housing further housing a demultiplexer.

13. The system of claim 10 wherein the connector housing further houses a serializer connected with the analog-to-digital converter.

14. The system of claim 10 wherein the connector housing further houses a processor, the processor operable to compress digital data responsive to output by the analog-to-digital converter.

15. An ultrasound probe for connection with an imaging system, the probe comprising:
    an ultrasound transducer in a first housing;
    a releasable connector electrically connected with the ultrasound transducer and releasably connectable with an ultrasound imaging system, the releasable connector having a plurality of electrical outputs for respective signals representing different elements; and
    a processor connected between the ultrasound transducer and the releasable connector, the processor in a second housing of the releasable connector and operable to compress signals from the ultrasound transducer, the first housing non-releasably connected to the second housing by a cable, the cable longer than a longest length of both the first and second housing, the second housing positioned against the ultrasound imaging system for the releasable connection with the ultrasound imaging system and when the releasable connector is connected for communicating from the analog-to-digital converter to the ultrasound imaging system.

16. The probe of claim 15 further comprising an analog-to-digital converter between the transducer and the processor, the processor comprising a digital processor.

17. The probe of claim 15 wherein the processor is operable to compress signals by partial beamforming.

18. A method for communicating signals from a transducer array to an imaging system, the method comprising:
  (a) releasably connecting a probe assembly to an imaging system;
  (b) transducing acoustic energy into electrical signals;
  (c) transmitting the electrical signals to an analog-to-digital converter;
  (d) converting the electrical signals into digital data within the probe assembly; and
  (e) passing the digital data from the probe assembly to at least a part of a beamformer of the imaging system;

wherein (c) comprises transmitting the electrical signals through a cable of the probe assembly, and wherein (d) comprises converting the electrical signals into digital data within a connector housing of the probe assembly, the connector housing separate from a probe housing housing transducers for performing (b), the probe assembly of the connector housing and probe housing being connected by the cable without any releasable connections, and the connector housing spaced from the probe housing by the cable, the cable outside of the connector and probe housings, where (a) comprises abutting the connector housing against a larger housing of the imaging system.

19. The method of claim 18 further comprising:
  (f) compressing the digital data prior to (e).

20. The method of claim 18 further comprising:
  (f) time division multiplexing the electrical signals prior to (c); and
  (g) demultiplexing the digital data after (d) and before (e).

21. The probe of claim 1 wherein transducer cables within the cable each have a constant length and same impedance.

* * * * *